United States Patent
Shon et al.

(10) Patent No.: US 9,492,595 B2
(45) Date of Patent: Nov. 15, 2016

(54) MEDICAL TUBE CATHETER AND METHOD FOR MANUFACTURING SAME

(71) Applicant: CEM TECH CO., LTD, Hwaseong-si (KR)

(72) Inventors: Dong Min Shon, Suwon-si (KR); Young Woo Lee, Hwaseong-si (KR); Seok Geun Park, Anseong-si (KR); Hee Jin Ka, Hwaseong-si (KR); Myoung Su Kim, Hwaseong-si (KR)

( * ) Notice: Subject to any disclaimer, the term of this patent is extended or adjusted under 35 U.S.C. 154(b) by 26 days.

(21) Appl. No.: 14/395,113

(22) PCT Filed: Apr. 17, 2013

(86) PCT No.: PCT/KR2013/003240
§ 371 (c)(1),
(2) Date: Oct. 17, 2014

(87) PCT Pub. No.: WO2013/157846
PCT Pub. Date: Oct. 24, 2013

(65) Prior Publication Data
US 2015/0119822 A1 Apr. 30, 2015

(30) Foreign Application Priority Data
Apr. 19, 2012 (KR) .......................... 10-2012-0040745

(51) Int. Cl.
*A61L 29/14* (2006.01)
*B29C 47/00* (2006.01)
(Continued)

(52) U.S. Cl.
CPC .............. *A61L 29/14* (2013.01); *A61L 29/049* (2013.01); *A61L 29/141* (2013.01); *A61L 29/143* (2013.01); *A61M 25/0009* (2013.01);
(Continued)

(58) Field of Classification Search
CPC .. A61L 29/14; A61M 25/00; B29C 47/0004; B29C 47/0023; B29C 47/0066; B29C 69/001; B29C 65/00; B29C 66/71; Y10T 428/139; Y10T 428/1393; B29D 23/00
USPC .................. 264/138, 150, 154; 156/293, 294
See application file for complete search history.

(56) References Cited

U.S. PATENT DOCUMENTS

2009/0324666 A1\* 12/2009 Krongauz ............... A61L 27/34
424/409

*Primary Examiner* — Walter B Aughenbaugh
(74) *Attorney, Agent, or Firm* — Antonio Ha & U.S. Patent, LLC

(57) ABSTRACT

The present invention relates to a medical tube catheter and to a method for manufacturing same. The medical tube catheter according to the present invention includes PVC resin (polyvinyl chloride resin), a plasticizer, a stabilizer, and NBR (acrylonitrile butadiene rubber). Also, the method for manufacturing the medical tube catheter according to the present invention comprises: a first step of preparing a composition by mixing 80 to 120 parts by weight of a plasticizer, 1 to 3 parts by weight of a stabilizer, and 3 to 20 parts by weight of NBR with respect to 100 parts by weight of PVC resin at room temperature; a second step of blending the composition at 140° C. to 170° C. into a blended compound; a third step of extruding the blended compound through an extruder into a tube shape; a fourth step of cooling the tube; and a fifth step of cutting the cooled tube into predetermined lengths. Accordingly, the product has the economic advantage and good physical properties of natural latex, while having good biocompatibility so as to prevent various allergies and side effects from toxins. Also, by adding NBR, elasticity is imparted and flexibility is improved, and slippage is improved so that insertion in and removal from the body is made easy and damage to a mucous membrane from stickiness can be prevented.

9 Claims, 3 Drawing Sheets

(51) Int. Cl.
- *B29C 69/00* (2006.01)
- *B29C 65/00* (2006.01)
- *A61L 29/04* (2006.01)
- *A61M 25/00* (2006.01)
- *B29D 23/00* (2006.01)
- B29K 27/06 (2006.01)
- B29K 105/00 (2006.01)
- B29K 19/00 (2006.01)
- B29K 627/06 (2006.01)
- B29L 31/00 (2006.01)

(52) U.S. Cl.
CPC .......... *B29C 47/0066* (2013.01); *B29C 65/00* (2013.01); *B29C 66/71* (2013.01); *B29C 69/001* (2013.01); *B29D 23/00* (2013.01); A61L 2400/10 (2013.01); B29C 47/0004 (2013.01); B29C 47/0023 (2013.01); B29C 2793/0027 (2013.01); B29K 2019/00 (2013.01); B29K 2027/06 (2013.01); B29K 2105/0038 (2013.01); B29K 2105/0044 (2013.01); B29K 2105/0088 (2013.01); B29K 2627/06 (2013.01); B29L 2031/7542 (2013.01); Y10T 29/49826 (2015.01); Y10T 428/139 (2015.01); Y10T 428/1393 (2015.01)

MEDICAL TUBE CATHETER AND METHOD FOR MANUFACTURING SAME

TECHNICAL FIELD

The present invention relates to a medical tube catheter, and more specifically, to a medical tube catheter that has economic advantages and good physical properties and that contains a good biocompatible material unlike the conventional natural latex material that may cause various allergies and contain various toxins harmful for the body.

BACKGROUND ART

In general, a catheter refers to a medical tube that is inserted into the body for drug delivery or that is used for discharging foreign substances from the body.

There are various types of catheters depending on the purposes thereof, which include, e.g., a urethral catheter inserted into the urethra to temporally discharge urine, a bronchial tube catheter used for discharging phlegm or saliva from the airway of the body, or a rectal tube catheter used for removing the foreign substances from the rectum.

Such a medical tube catheter is directly inserted into the body upon use, and thus, the material of the catheter needs to satisfy various conditions including flexibility, dimensional stability, and processability. Most of all, biocompatibility is critical for the medical tube catheter.

Natural latex has been widely used as the material of the conventional medical tube catheters.

Latex, a natural substance produced from the rub tree, is processed and used for up to 40,000 products including shoes, gloves, sportswear, and medical products, thanks to low price and relatively good physical properties. However, latex may cause allergies and contain a number of toxins. Accordingly, latex is disadvantageous in light of biocompatibility.

For example, a latex catheter, when directly contacting the human body, may cause skin allergies, such as dermatitis or rash, on the contacted region, or if inhaling latex-contained particles, one may have a sneeze, nasal discharge or congestion or other nasal inflammation or spasmodic dyspnea or cough. In severe cases, anaphylaxis (spasmodic dyspnea, chest compression, hypotension or shocks, etc.) may be caused, leading to a serious condition.

In particular, such catheter performs hole punching to facilitate drainage, and in this case, the catheter may directly discharge various toxins, affecting the human body.

As an alternative, there has been an attempt to replace latex with polyurethane, silicone, or synthetic polyisoprene (Korean Patent Application Publication No. 10-2011-0037929) as the material of the tube catheter.

However, polyurethane is relatively pricey, silicone suffers from low processability together with relatively high price, and synthetic polyisoprene is disadvantageous in light of price and is difficult to commercialize due to its material properties.

Meanwhile, as set forth in Korean Patent Application Publication No. 10-2000-22224 titled "medical equipment"), there has been an attempt to utilize PVC (polyvinylchloride) as the material of the catheter.

However, a plasticizer is additionally used to lower the hardness of the PVC material. Such use of the plasticizer may reduce the hardness of the PVC but may also lead the surface of the catheter to be sticky. Accordingly, such type of catheter is difficult to insert and remove from the body due to friction. Thus, the catheter is nearly impossible to use, and forced use of the catheter may damage the contacting region.

Further, in the above case, the hardness can be lowered by adding a plasticizer, but elasticity cannot be obtained, thus rendering it difficult to replace the conventional latex material therewith.

SUMMARY

Objects

An object of the present invention is to provide a medical tube catheter that has economic advantages and good physical properties of natural latex, while having good biocompatibility so as to prevent various allergies and side effects from toxins and a method of manufacturing the same.

Further, an object of the present invention is to provide a medical tube catheter that, by adding NBR, may impart elasticity and improve flexibility and may improve slippage so that insertion in and removal from the body is made easy and may prevent damage to a mucous membrane from stickiness.

Configuration

The above objects are achieved by a medical tube catheter according to an embodiment of the present invention, comprising a PVC (Polyvinyl chloride) resin, a plasticizer, a stabilizer, and NBR (acrylonitrile butadiene rubber).

Here, with respect to 100 parts of weight of the PVC resin, 80 to 120 parts of weight of the plasticizer, 1 to 3 parts of weight of the stabilizer, and 3 to 20 parts of weight of the NBR.

Preferably, with respect to 100 parts of weight of the PVC resin, the plasticizer may contain 95 to 105 parts of weight and the NBR may contain 10 to 15 parts of weight.

Here, the NBR may be prepared as an NBR mixture obtained by blending NBR and PVC.

The NBR mixture may be blended to include 85 to 95 weight % of NBR and 5 to 15 weight % of PVC Meanwhile, 0.8 to 1.2 parts of weight of a lubricant with respect to 100 parts of weight of the PVC resin may be further included.

Meanwhile, the above objects may be achieved by a method for manufacturing a medical tube catheter according to another embodiment of the present invention, the method comprising: a first step of preparing a composition by mixing 80 to 120 parts by weight of a plasticizer, 1 to 3 parts by weight of a stabilizer, and 3 to 20 parts by weight of NBR with respect to 100 parts by weight of a PVC resin at room temperature; a second step of blending the composition at 140° C. to 170° C. into a blended compound; a third step of extruding the blended compound through an extruder into a tube shape; a fourth step of cooling the tube; and a fifth step of cutting the cooled tube into predetermined lengths.

The first step may include a step of forming an NBR mixture by blending 85 to 95 weight % of NBR and 5 to 15 weight % of PVC; and a step of mixing the NBR mixture with the PVC resin, the plasticizer, and the stabilizer to form a mixture.

Meanwhile, in the first step, 0.8 to 1.2 parts of weight of a lubricant with respect to 100 parts of weight of the PVC resin may be further included.

Meanwhile, the method may further comprise: a sixth step of forming a hole in an end of the cut tube; a seventh step of trimming both cut end surfaces of the tube; and an eight step of coupling a connector to the tube.

Effects

By a medical tube catheter having the above-described structure and a method of manufacturing the same according to the present invention, the medical tube catheter has the economic advantage and good physical properties of natural latex, while having good biocompatibility so as to prevent various allergies and side effects from toxins.

Also, by adding NBR, elasticity is imparted and flexibility is improved, and slippage is improved so that insertion in and removal from the body is made easy and damage to a mucous membrane from stickiness can be prevented.

DESCRIPTION OF EXEMPLARY EMBODIMENTS

Figure 1:
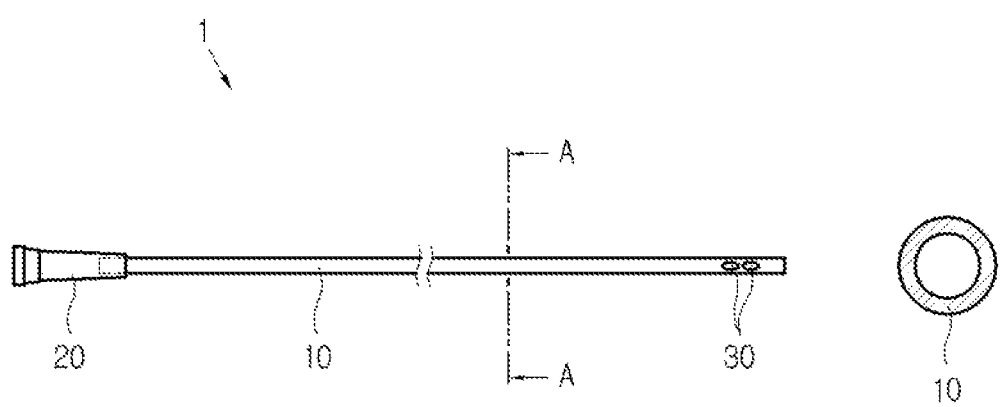
FIG. 1 is a side view illustrating a medical tube catheter according to an embodiment of the present invention.

Hereinafter, the present invention is described in detail with reference to the accompanying drawings.

According to an embodiment of the present invention, a medical tube catheter 1 includes a PVC (Polyvinyl chloride) resin, a plasticizer, a stabilizer, and NBR (acrylonitrile butadiene rubber).

Preferably, with respect to 100 parts of weight of the PVC resin, 70 to 130 parts of weight of the plasticizer, 1 to 3 parts of weight of the stabilizer, 3 to 20 parts of weight of the NBR, and 1 part of weight of a lubricant and other additives are prepared.

The composition ratio is represented with respect to 100 parts of weight of the PVC resin as in the following table:

TABLE 1

| First embodiment: | | |
| --- | --- | --- |
| | Parts of weight (phr) | weight % |
| PVC resin | 100 | 40-60 |
| plasticizer | 80-120 | 40-60 |
| NBR | 3-20 | 3-15 |
| stabilizer | 1-3 | 0.5-1.5 |
| lubricant and others | 0.8-1.2 | 0.1-1 |

In this embodiment, the plasticizer is added to a high-molecular material such as the PVC resin to impart plasticity, enhance prossessability, and vary physical properties to allow it to have good characteristics. The plasticizer is typically used for reinforcing flexibility, cold resistance, volatile resistance, and electrical characteristics.

Various types of plasticizers may be put to use. For example, phthalate plasticizers, such as DEHP (or POP; Di-EthylHexyl Phthalate) or DINP(Diisononyl-phthalate), may be used.

Or, as non-DEHP (DOP), TOTM (Tri Ethyl-hexyl {also referred to as Octyl}Triellitate) may be used as well. The latter material may be widely used in medical materials.

According to the present invention, the plasticizer may be prepared preferably by 80-120 parts of weight with respect to 100 parts of weight of the PVC resin.

As the amount of the plasticizer decreases, a lowering in the hardness by the PVC resin is not achieved. In contrast, if the amount exceeds the above, flexibility may be enhanced but stickiness may be excessively increased.

More preferably, the plasticizer may be prepared by 95 to 105 parts of weight with respect to 100 parts of weight of the PVC resin.

TABLE 2

| Second embodiment: | | |
| --- | --- | --- |
| | Parts of weight (phr) | weight % |
| PVC resin | 100 | 40-60 |
| plasticizer | 95-105 | 40-60 |
| NBR | 10-15 | 8-15 |
| stabilizer | 1-3 | 0.5-1.5 |
| lubricant and others | 1 | 0.1-1 |

The applicants found from repeated experiments that when the plasticizer contains 100 parts of weight per 100 parts of weight of the PVC resin, the most appropriate physical properties are attained.

According to the present invention, the NBR is used for enhancing feeling of touch, elasticity, flexibility, slippage, and tearing strength while decreasing the migration of plasticizer.

In other words, this is why although the plasticizer can enhance flexibility of the medical tube catheter 1, the flexibility alone is insufficient for use in the airway or urethra with various bends and elasticity needs to be enhanced as well.

Meanwhile, the NBR decreases the surface stickiness that occurs due to addition of the plasticizer. That is, as described above, more content of the plasticizer needs to be added to lower the hardness of the PVC resin to impart flexibility, but this also leads to an increase in the stickiness. Accordingly, the content of the plasticizer is forced Lobe limited.

However, according to the present invention, the NBR, together with the plasticizer, is added to decrease the stickiness that occurs due to the plasticizer, thus easing the restriction on the content of the plasticizer. Further, the stickiness may be minimized in the same content of plasticizer. Accordingly, upon use of the mobile communication terminal 1, high usability may be ensured while preventing damage to a mucous membrane.

The NBR may be prepared by 3-20 parts of weight with respect to 100 parts of weight of the PVC resin as in the first embodiment.

More preferably, the NBR may be prepared by 10-15 parts of weight with respect to 100 parts of weight of the PVC resin as in the second embodiment.

In the above composition ratio of the NBR, if the content of the NBR is increased, the slippage and feeling of touch of the medical tube catheter 1 are enhanced so much, whereas thermal resistance is decreased and blendability with the PVR resin is deteriorated. Further, when the composition is blended at 140 to 170° C. to form a compound or is extruded, the fused plasticizer or NBR may be attached to a screw or wall of the molding, thus deteriorating the processability.

Accordingly, applicants found from repeated experiments a mixture ration at which compatibility with the PVC resin is maintained and a lowering in the processability is minimized while the slippage and feeling of touch are satisfied.

Meanwhile, according to the present invention, as an alternative to the NBR, a mixture of NBR and PVC may be used to enhance compatibility with the PVC resin.

That is, the NBR mixture has the advantages of both NBR and PVC. Further, the NBR mixture already contains PVC and thus is easily blended with the PVC resin, thus leading to better compatibility.

The NRB mixture may be prepared at various mixture rations between NBR and PVC. For example, 85 to 95 weight % of NBR and 5 to 15 weight % of PVC may be blended with each other.

Meanwhile, a known NRB mixture may be used, such as, e.g., NBR7030S and NBR8300 (Product Name) commercially available from LG Chem, Ltd.

NBR7030S contains 29 weight % or more of NBR and 67 weight % or more of a PVC mixture and has similar flexibility and elasticity to vulcanized rubber even without being vulcanized. In particular, NBR7030S has good oil resistance, chemical resistance, and anti-slip property. Further, NBR7030S is excellent in the feeling of touch as compared with flexible PVC, particularly in elasticity, anti-slip property, and tearing strength. Further, NBR7030S has a low migration of plasticizer and thus provides good durability.

Further, NBR7030S may be subjected to a typical method for processing a thermo-plastic resin and may be thus extruded and injected. Further, NBR7030S, thanks to its good flowability, may be processed at a relatively low temperature.

Meanwhile, NBR8300 is obtained by mixing about 90 weight % of NBR and about 10 weight % of PVC, and this is a partially cross-linked elastic body having a power-shaped polar group. NRB8300 is easily mixed with other polymer and has excellent compatibility with PVC, so that, upon use, it may be mixed with up to 100 parts of weight of PVC, plasticizer, filler, and thermal and UV stabilizer, pigment, etc. A mixture of NBR8300 and PVC may reinforce oil resistance and fuel oil resistance, as well as elasticity, thus enhancing impact resistance and texture of PVC.

The stabilizer is used for enhancing the processability of the PVC resin, preventing damage to the PVC resin upon process, and preventing a deterioration of the product.

As the stabilizer, either a metallic stabilizer such as calcium (Ca) and zinc (Zn) or a non-metallic stabilizer, such as a phenol-based or phosphor-based stabilizer may be put to use. In this case, Tin-based, Pb-based, Cd-based, and Ba-based stabilizers have low biocompatibility to the human body and are thus preferably avoided from being in use.

As the lubricant, an internal lubricant that functions to reduce heat generation between the resins upon process and an external lubricant that functions to lubricate a metallic portion (e.g., screw or head, etc.) contacting the resin may be used, and the lubricant may be prepared by 8.0 to 1.2 parts of weight per 100 parts of weights of PVC resin.

Hereinafter, a method for manufacturing a medical tube catheter according to the present invention is described with reference to FIGS. 2 and 3.

Figure 2:
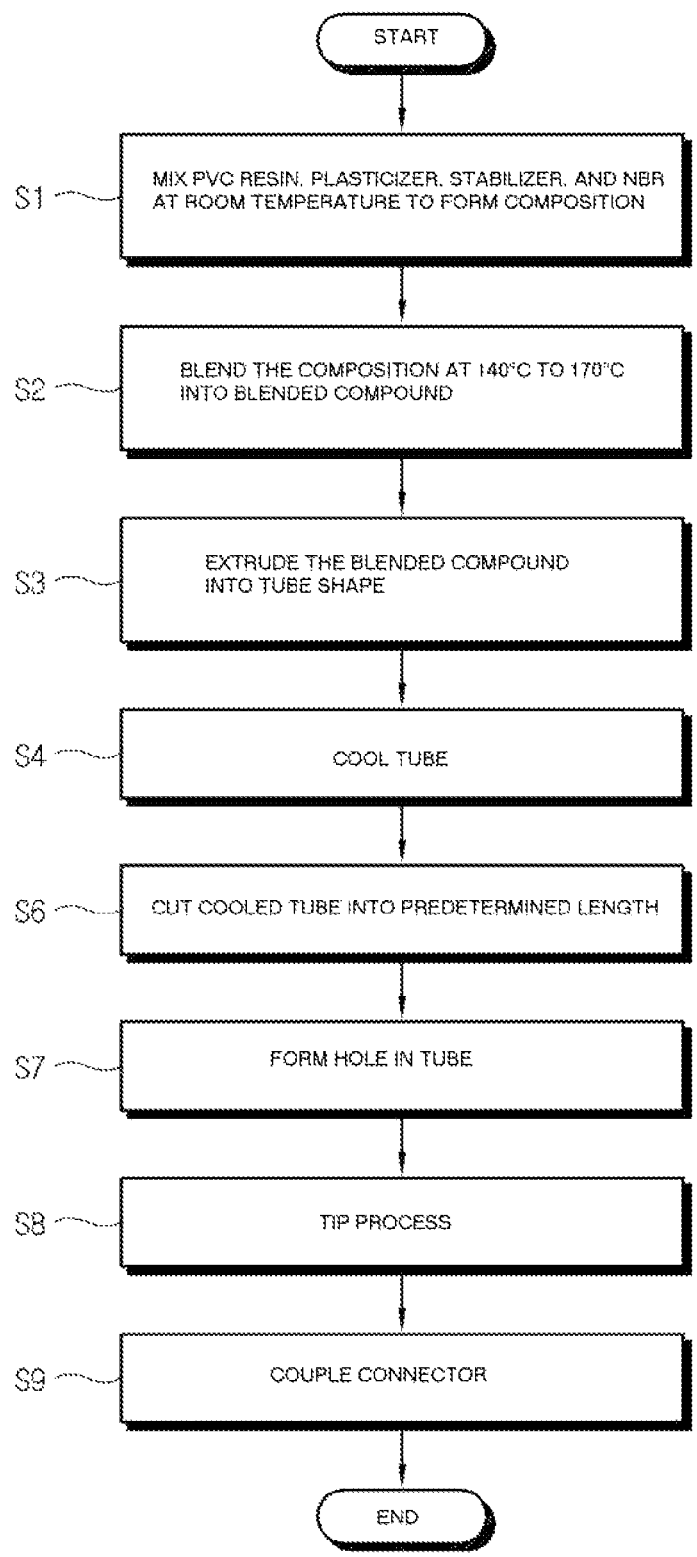
FIG. 2 is a flowchart illustrating a method of manufacturing a medical tube catheter according to an embodiment of the present invention.

Referring to FIG. 2, according to an embodiment of the present invention, a method for manufacturing a medical tube catheter comprises a first step (S1) of preparing a composition by mixing 80 to 120 parts by weight of a plasticizer, 1 to 3 parts by weight of a stabilizer, and 3 to 20 parts by weight of NBR with respect to 100 parts by weight of a PVC resin at room temperature; a second step (S2) of blending the composition at 140° C. to 170° C. into a blended compound; a third step (S3) of extruding the blended compound through an extruder into a tube shape; a fourth step (S4) of cooling the tube; and a fifth step (S5) of cutting the cooled tube into predetermined lengths.

In the first step (S1), the PVC resin may be prepared, e.g., in powder state, the plasticizer in liquid state, the stabilizer in powder or liquid state, and NBR in powder state. After mixed in the first step (S1), the composition is blended at about 150° C. in the second step (S2), thus forming pallet-shaped granules.

Figure 3:
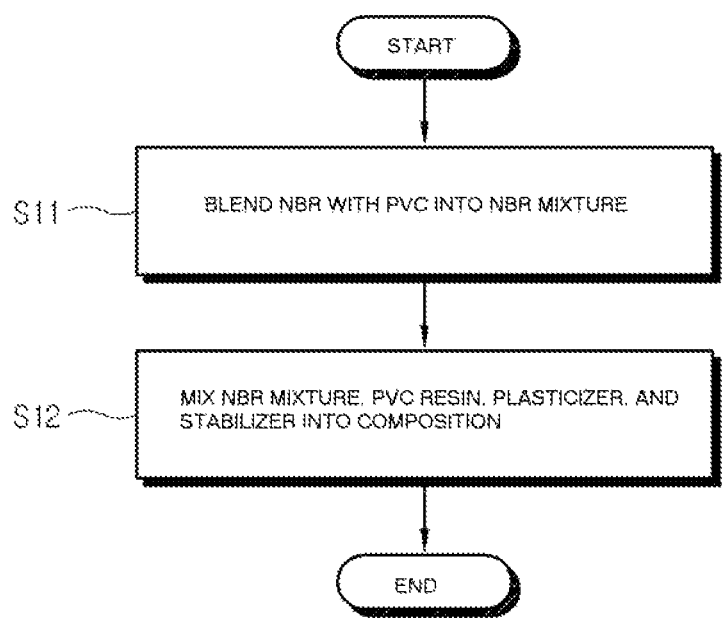
FIG. 3 is a flowchart illustrating a method of manufacturing a medical tube catheter according to another embodiment of the present invention.

Here, the first step (S1), as shown in FIG. 3, may include a step (S11) of forming an NBR mixture by blending 85 to 95 weight % of NBR and 5 to 15 weight % of PVC and a step (S12) of mixing the NBR mixture with the PVC resin, the plasticizer, and the stabilizer to form a mixture.

Meanwhile, in the first step, 0.8 to 1.2 parts of weight of a lubricant with respect to 100 parts of weight of the PVC resin may be further included.

After the fifth step (S5), an additional step may be performed depending on the purposes of the medical tube catheter 1.

For example, in the case of the nelaton catheter shown in FIG. 1, the method may further comprise a sixth step (S6) of forming a hole 30 in an end of the cut tube 10; a seventh step (S7) of trimming sharp cut surfaces at both ends of the tube 10; and an eight step (S8) of coupling a connector 20 to the tube 10.

Additionally, a step of printing a mark that allows for indication of a depth to which the catheter is inserted and a step of putting the manufactured catheter 1 in a sterile wrapping paper, and sealing and sterilizing the same.

INDUSTRIAL AVAILABILITY

By a medical tube catheter having the above-described structure and a method of manufacturing the same according to the present invention, the medical tube catheter has the economic advantage and good physical properties of natural latex, while having good biocompatibility so as to prevent various allergies and side effects from toxins.

Also, by adding NBR, elasticity is imparted and flexibility is improved, and slippage is improved so that insertion in and removal from the body is made easy and damage to a mucous membrane from stickiness can be prevented.

The invention claimed is:

1. A medical tube catheter, comprising a PVC (Polyvinyl chloride) resin, a plasticizer, a stabilizer, and NBR (acrylonitrile butadiene rubber), wherein with respect to 100 parts of weight of the PVC resin, 80 to 120 parts of weight of the plasticizer, 1 to 3 parts of weight of the stabilizer, and 3 to 20 parts of weight of the NBR are included in the medical tube catheter.

2. The medical tube catheter of claim 1, wherein with respect to 100 parts of weight of the PVC resin, the plasticizer contains 95 to 105 parts of weight and the NBR contains 10 to 15 parts of weight.

3. The medical tube catheter of claim 1, wherein the NBR is an NBR mixture obtained by blending NBR and PVC.

4. The medical tube catheter of claim 3, wherein the NBR mixture is obtained by blending 85 to 95 weight % of NBR and 5 to 15 weight % of PVC.

5. The medical tube catheter of claim 2, further comprising 0.8 to 1.2 parts of weight of a lubricant with respect to 100 parts of weight of the PVC resin.

6. A method for manufacturing a medical tube catheter, the method comprising: a first step of preparing a composition by mixing 80 to 120 parts by weight of a plasticizer, 1 to 3 parts by weight of a stabilizer, and 3 to 20 parts by weight of NBR with respect to 100 parts by weight of a PVC resin at room temperature; a second step of blending the composition at 140° C. to 170° C. into a blended compound; a third step of extruding the blended compound through an extruder into a tube shape; a fourth step of cooling the tube; and a fifth step of cutting the cooled tube into predetermined lengths.

7. The method of claim 6, wherein the first step includes forming an NBR mixture by blending 85 to 95 weight % of NBR and 5 to 15 weight % of PVC and mixing 3 to 20 parts by weight of the NBR mixture with 100 parts by weight of the PVC resin, 80 to 120 parts by weight of the plasticizer, and 1 to 3 parts by weight of the stabilizer to form a mixture.

8. The method of claim 6, wherein the first step further includes 0.8 to 1.2 parts of weight of a lubricant with respect to 100 parts of weight of the PVC resin.

9. The method of claim 6, further comprising: a sixth step of forming a hole in an end of the cut tube; a seventh step of trimming both cut end surfaces of the tube; and an eighth step of coupling a connector to the tube.

\* \* \* \* \*